United States Patent [19]

Freedman

[11] 3,969,360

[45] July 13, 1976

[54] CATALYZED ALKYLATION OF HALOPYRIDINATES

[75] Inventor: Harold H. Freedman, Newton Center, Mass.

[73] Assignee: The Dow Chemical Company, Midland, Mich.

[22] Filed: Dec. 23, 1974

[21] Appl. No.: 535,249

[52] U.S. Cl............................................ 260/295 R
[51] Int. Cl.$^2$........................................ C07D 213/26
[58] Field of Search ................................ 260/295 R

[56] References Cited
UNITED STATES PATENTS

| | | | |
|---|---|---|---|
| 3,609,158 | 9/1971 | Torba............................ | 260/295 R |
| 3,755,339 | 8/1973 | McKendry...................... | 260/295 R |
| 3,761,486 | 9/1973 | McGregor...................... | 260/295 R |
| 3,862,952 | 1/1975 | Markley......................... | 260/295 R |
| 3,883,541 | 5/1975 | Hamilton........................ | 260/295 R |

Primary Examiner—Norman A. Drezin
Attorney, Agent, or Firm—L. Wayne White

[57] ABSTRACT

The reaction between the alkali metal halopyridinates with the lower alkyl esters of α-chloro or bromo acetic acid (or propionic acid) to form the corresponding O-alkylated halopyridinates is catalyzed by quaternary ammonium salts. For example, methyl α-(6-chloropyridinyloxy)acetate was prepared in excellent yield by reacting sodium 6-chloropyridinate with excess methyl α-chloroacetate in the presence of 2 mole percent of benzyl triethyl ammonium chloride.

10 Claims, No Drawings

CATALYZED ALKYLATION OF HALOPYRIDINATES

BACKGROUND OF THE INVENTION

The O-alkylated halopyridinates corresponding to Formula I are a known class of herbicides.

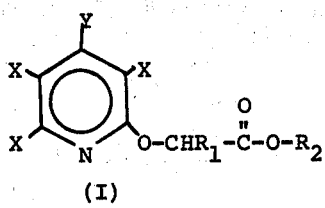

(I)

In I, each X is independently hydrogen or halo and at least one X is halo (i.e., fluoro, chloro, bromo or iodo); Y is hydrogen, halo or NR'R'' wherein R' and R'' are each independently hydrogen or lower alkyl of 1 to 4 carbon atoms; $R_1$ is hydrogen or methyl; and $R_2$ is lower alkyl. As used herein, the term "lower alkyl" shall mean an alkyl radical of from 1 to 4 carbon atoms (i.e., methyl, ethyl, propyl and butyl).

Compounds of Formula I have been prepared by reacting (a) an alkali metal halopyridinate corresponding to the formula

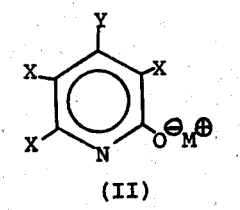

(II)

wherein M is an alkali metal and X and Y have the aforesaid meaning, with (b) a lower alkyl ester of α-chloro or bromo acetic acid (or propionic acid) corresponding to the formula

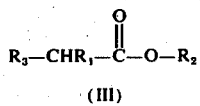

(III)

wherein $R_1$ and $R_2$ have the aforesaid meaning and $R_3$ is chloro or bromo. The reaction has been conducted under various and miscellaneous reaction conditions and has been plagued by the low reaction rates, concurrent formation of N-alkylated by-products, and so forth.

SUMMARY OF THE INVENTION

It has now been discovered that compounds of Formula I can be prepared in excellent yield and purity by reacting II in solid particulate form with III in an inert organic liquid reaction medium under alkaline conditions and in the presence of a quaternary ammonium salt catalyst.

DETAILED DESCRIPTION OF THE INVENTION

The catalysts: Essentially any compound from the known class of quaternary ammonium compounds can be used in the instant invention. Suitable quaternary ammonium salts have a minimum solubility of at least about 1 weight percent in the liquid reaction medium at 25°C and normally have a total aggregate carbon content of at least about 10 carbon atoms and preferably from about 12 to about 31 carbon atoms. The ammonium salts can be represented by the formula $R_1'R_2'R_3'R_4'N^+A^-$, where $R_{40}'-R_4'$ are hydrocarbyl groups (e.g., alkyl, aryl, alkaryl, aralkyl, cycloalkyl, etc.). Additionally, $R_1'$ can join with $R_2'$ to form a 5- or 6-membered heterocyclic compound having at least 1 quaternized nitrogen atom in the ring and may also contain one non-adjacent atom of nitrogen, oxygen or sulfur within the ring. Typically, $R_1'-R_4'$ are hydrocarbyl groups of from 1 to about 12 carbon atoms. $A^-$ is an inert neutralizing anion and may be varied to convenience. Chloride and bromide are the preferred anions but other suitable anions include, for example, fluoride, iodide, bisulfate, perchlorate, nitrate, acetate, benzoate, tosylate, etc. The following compounds are illustrative: tetraalkylammonium salts, such as tetra-n-butyl-, tetrahexyl-, tri-n-butylmethyl-, and trioctylmethyl- and tridecylmethyl-ammonium chlorides, bromides, bisulfates, tosylates, etc.; aralkyl ammonium salts, such as tetrabenzyl ammonium chloride, benzyltrimethyl-, benzyltriethyl-, benzyltributyl-, and then ethyltrimethyl ammonium chlorides, bromides, etc.; aryl ammonium salts, such as triphenylmethyl ammonium fluoride, chloride or bromide, N,N,N-trimethylaniliniumbromide, N,N-diethyl-N-ethylaniliniumbisulfate, trimethylnapthylammonium chloride, p-methylphenyl trimethyl ammonium chloride or tosylate, etc.; 5- and 6-membered heterocyclic compounds containing at least one quaternized nitrogen atom in the ring, such as N-methylpyridinium chloride or methyl sulfate, N-hexylpyridinium iodide, 4-pyridyltrimethyl ammonium iodide, 1-methyl-1-azabicyclo[2.2.1]heptane bromide, N,N-dibutyl morpholinium chloride, N-ethylthiazolium chloride, N-butylpyrrolium chloride, etc., and other like compounds.

The preferred catalysts are benzyltrimethyl-, benzyltriethyl- and tetra-n-butylammonium salts.

The quaternary ammonium salts are used in the process in small but catalytic amounts. For example, satisfactory reaction rates have been achieved using the ammonium salts in amounts from about 0.25 to about 20 mole percent, based on the reactants, but amounts of from 0.5 to about 10 mole percent are generally preferred.

The reactants: The reactants in this process comprise two well-known classes of reactants.

The alkali metal halopyridinates are represented by Formula II. The sodium and potassium salts and particularly the sodium salts of such halopyridinates are preferred.

The lower alkyl esters of α-chloro or bromo acetic acid (or propionic acid) are likewise well known. In this particular instance, the lower alkyl esters of α-chloro acetic acid are the preferred reactants and the methyl and ethyl esters of α-chloro acetic acid are the most preferred reactants.

Obviously, one skilled in the art will be able to select the appropriate reactants within groups II and III above to produce any particular compound within I. Suitable combinations will be further illustrated, however, in the Examples below.

Process parameters: The process is conducted in an inert organic liquid reaction medium under alkaline conditions and preferably with efficient blending. By the term "an inert inorganic liquid reaction medium" we mean to include any organic liquid which is inert in the reaction and does not react with either reactants II or III or with the final product I. Suitable such solvents include conventional hydrocarbon solvents (e.g., hexane, benzene, toluene, xylene, etc.) and chlorinated hydrocarbon solvents (e.g., methylene chloride, methyl chloroform, perchloroethylene, etc.) and other like solvents. Also included within the stated term is the use of the lower alkyl esters of α-chloro or bromo acetic acid (or propionic acid) in excess as the liquid reaction medium. The use of the latter compounds as the liquid reaction medium is preferred.

The alkaline conditions of the reacting mixture may be established by the addition of an alkali or alkaline earth metal, oxide or hydroxide, or the like to the reaction mixture or, the alkaline conditions may be established merely by the presence of the alkali metal halopyridinate.

The following Examples will further illustrate the invention.

EXAMPLE 1

Essentially equimolar amounts of sodium 3,5,6-trichloropyridinate and methyl α-chloroacetate in toluene were blended together in the presence of from 2 to 5 mole percent of benzyltriethylammonium chloride and the mixture refluxed at 105°C for 3 hours. The product, methyl α-(3,5,6-trichloropyridyl)acetate, was thus obtained in approximately 90 percent yield.

EXAMPLE 2

Sodium 6-chloropyridinate and excess methyl α-chloroacetate were blended together with 2 mole percent of benzyltriethylammonium chloride and the mixture warmed at 50°C for 0.5 hours. The product, methyl α-(6-chloropyridyloxy)acetate was thus obtained in 95 percent yield. In the absence of catalyst, very little reaction occurred.

Other compounds within the scope of Formula I can be likewise produced using the same quaternary ammonium catalyst or other quaternary ammonium catalysts having the aforesaid properties. For example, tetra-n-butyl ammonium chloride could have been used in Examples 1 and 2 above to give similar results. In like manner, ethyl α-(3,5-dichloro-6-fluoropyridyloxy)acetate can be prepared by reacting the appropriate reactants in II and III together in the presence of benzyltrimethylammonium chloride, benzyltriethylammonium chloride, tetra-n-butylammonium bisulfate, etc. Ethyl α-(3,5-dichloro-6-fluoro-4-aminopyridyloxy)acetate can be prepared by mixing the appropriate reactants from II and III with benzyltriethylammonium chloride or bromide, benzyltrimethylammonium chloride, tetrabutylammonium bisulfate or chloride, etc. Other compounds can be similarly prepared.

What is Claimed is:

1. In the process of preparing a compound corresponding to the formula

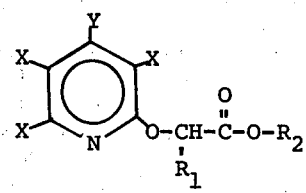

wherein:

X independently in each occurrence is hydrogen or halo and at least one X is halo;
Y is hydrogen, halo or —NR'R'' wherein R' and R'' are each independently hydrogen or lower alkyl;
R₁ is hydrogen or methyl; and
R₂ is lower alkyl;

by reacting in an inert organic liquid reaction medium under alkaline conditions and with efficient blending (a) a compound corresponding to the formula (a) 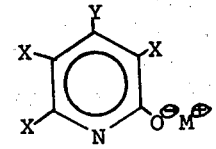

wherein M is an alkali metal and X and Y have the aforesaid meaning, in solid particulate form with (b) a compound dissolved in said liquid reaction medium and corresponding to the formula R₃CH(R₁)—C(O)—O—R₂, wherein R₁ and R₂ have the aforesaid meaning and R₃ is chloro or bromo;

the improvement consisting of conducting the process in the presence of a small but catalytic amount of a quaternary ammonium salt having a minimum solubility of at least one weight percent in the liquid reaction medium at 25°C and having a total aggregate carbon content of at least about 10 carbon atoms.

2. The process defined by claim 1 wherein said quaternary ammonium salt corresponds to the formula R₁'R₂'R₃'R₄'N⁺A⁻, wherein R₁'–R₄' are hydrocarbyl groups or, R₃' and R₄' are hydrocarbyl groups while R₁' and R₂' are joined to form a 5- or 6-membered heterocyclic ring having at least 1 quaternized nitrogen atom in the ring as the first member thereof, a second member thereof is a carbon atom or a non-adjacent atom of nitrogen, oxygen, or sulfur, and the remaining members of the ring are each carbon atoms; A⁻ is an inert neutralizing anion.

3. The process defined by claim 2 wherein R₁'–R₄' are each independently hydrocarbyl groups of from 1 to about 12 carbon atoms.

4. The process defined by claim 3 wherein said quaternary ammonium salt has a total aggregate carbon content of from about 12 to about 13 carbon atoms.

5. The process defined by claim 4 wherein A⁻ is chloride or bromide.

6. The process defined by claim 1 wherein said quaternary ammonium salt is a benzyltrimethyl-, a benzyltriethyl-, or a tetra-n-butylammonium salt.

7. The process defined by claim 1 wherein said quaternary ammonium salt is included in amounts of from about 0.25 to about 20 mole percent.

8. The process defined by claim 7 wherein said quaternary ammonium salt is included in amounts of from about 0.5 to about 10 mole percent.

9. The process defined by claim 7 wherein M is sodium or potassium; R₁ is hydrogen; R₂ is methyl or ethyl; R₃ is chloro; the molar ratio of (b) to (a) is at least one; and said quaternary ammonium salt is a benzyltrimethyl-, a benzyltriethyl-, or a tetra-n-butylammonium salt.

10. The process defined by claim 9 wherein (a) is sodium 3,5,6-trichloropyridinate or sodium 6-chloropyridinate; R₂ is methyl; and said quaternary ammonium salt is benzyltriethylammonium chloride which is included in amounts of from about 0.5 to about 10 mole percent.

* * * * *

UNITED STATES PATENT AND TRADEMARK OFFICE
CERTIFICATE OF CORRECTION

PATENT NO. : 3,969,360
DATED : July 13, 1976
INVENTOR(S) : Harold H. Freedman

It is certified that error appears in the above–identified patent and that said Letters Patent are hereby corrected as shown below:

Column 2, line 7: "$R_{40}'-R_4'$" should read --$R_1'-R_4'$--.

Column 4, line 45, Claim 4, line 3: "13" should read --31--.

Signed and Sealed this

Twenty-eighth Day of December 1976

[SEAL]

Attest:

RUTH C. MASON
*Attesting Officer*

C. MARSHALL DANN
*Commissioner of Patents and Trademarks*